(12) United States Patent
Pelletier et al.

(10) Patent No.: US 10,428,649 B2
(45) Date of Patent: Oct. 1, 2019

(54) FREQUENCY SENSORS FOR USE IN SUBTERRANEAN FORMATION OPERATIONS

(71) Applicant: Halliburton Energy Services, Inc., Houston, TX (US)

(72) Inventors: Michael T. Pelletier, Houston, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 230 days.

(21) Appl. No.: 15/540,250

(22) PCT Filed: Sep. 30, 2016

(86) PCT No.: PCT/US2016/054723
§ 371 (c)(1),
(2) Date: Jun. 27, 2017

(87) PCT Pub. No.: WO2018/063309
PCT Pub. Date: Apr. 5, 2018

(65) Prior Publication Data
US 2018/0328172 A1 Nov. 15, 2018

(51) Int. Cl.
*G01N 29/036* (2006.01)
*E21B 49/08* (2006.01)
(Continued)

(52) U.S. Cl.
CPC ............ *E21B 49/08* (2013.01); *E21B 47/10* (2013.01); *E21B 49/082* (2013.01);
(Continued)

(58) Field of Classification Search
CPC ...... E21B 49/08; E21B 49/082; E21B 49/086; G01N 29/036; G01N 2291/0226;
(Continued)

(56) References Cited

U.S. PATENT DOCUMENTS

| 4,817,430 A | * | 4/1989 | Benes | G01B 7/066 324/71.5 |
| 4,905,701 A | * | 3/1990 | Cornelius | G01N 29/022 422/68.1 |

(Continued)

FOREIGN PATENT DOCUMENTS

| EP | 0072744 A2 | * | 2/1983 | ........... G01N 29/036 |
| EP | 1254352 b1 | | 8/2006 | |
| WO | WO-2007143474 A1 | * | 12/2007 | ............. E21B 47/10 |

OTHER PUBLICATIONS

Raffa et al., "Model Validation of a Mercury Sensor, Based on the Resistivity Variation of a Thin Gold Film," Sensors and Actuators B: Chemical vol. 114, Issue 1, 2006, pp. 513-521.

(Continued)

*Primary Examiner* — David J Bolduc
(74) *Attorney, Agent, or Firm* — Gilliam IP PLLC

(57) ABSTRACT

The present disclosure relates to vibration frequency sensors comprising a vibratable flow tube having an interior for receiving a fluid, a vibration detector coupled to the flow tube for detecting a frequency of the fluid received by the flow tube during vibration thereof; and measurement circuitry coupled to the vibration detector for determining a frequency shift over time of the detected frequency. At least a portion of a surface of the interior of the flow tube is functionalized with a reactant sensitive to the analyte, and the frequency shift corresponds to the presence of the analyte, the analyte having reacted with the reactant.

20 Claims, 4 Drawing Sheets

(51) Int. Cl.
*E21B 47/10* (2012.01)
*G01N 33/28* (2006.01)

(52) U.S. Cl.
CPC ......... *E21B 49/086* (2013.01); *G01N 29/036* (2013.01); *G01N 33/2823* (2013.01); *G01N 2291/021* (2013.01); *G01N 2291/0226* (2013.01); *G01N 2291/0228* (2013.01); *G01N 2291/0256* (2013.01)

(58) Field of Classification Search
CPC ..... G01N 2291/0228; G01N 2291/021; G01N 2291/0256; G01N 2291/036
See application file for complete search history.

(56) References Cited

U.S. PATENT DOCUMENTS

| | | | | |
|---|---|---|---|---|
| 4,999,284 | A * | 3/1991 | Ward | G01N 29/036 204/403.1 |
| 5,501,986 | A * | 3/1996 | Ward | G01N 29/036 436/525 |
| 5,756,898 | A * | 5/1998 | Diatschenko | G01B 17/02 73/40.5 A |
| 5,796,012 | A | 8/1998 | Gomi et al. | |
| 5,853,994 | A * | 12/1998 | Gopinathan | G01N 29/032 435/6.11 |
| 5,985,673 | A | 11/1999 | Bao et al. | |
| 6,526,828 | B1 * | 3/2003 | Dayan | G01G 3/13 73/24.01 |
| 6,723,516 | B1 * | 4/2004 | Tom-Moy | G01N 29/036 422/82.01 |
| 7,025,138 | B2 | 4/2006 | Kurkjian et al. | |
| 7,063,981 | B2 * | 6/2006 | Bondestram | C23C 16/4402 118/715 |
| 7,360,399 | B2 * | 4/2008 | Schmidt | G01N 11/162 73/32 A |
| 7,875,455 | B1 * | 1/2011 | Li | E21B 47/06 422/82.02 |
| 8,004,669 | B1 * | 8/2011 | Kim | G01N 21/11 356/244 |
| 8,771,603 | B2 | 7/2014 | Harless et al. | |
| 8,973,427 | B2 * | 3/2015 | Jarrell | G01N 9/002 73/32 A |
| 9,000,942 | B2 * | 4/2015 | Atkinson | E21B 47/123 166/254.2 |
| 9,759,556 | B2 * | 9/2017 | Davis | G01B 17/025 |
| 2002/0178805 | A1 * | 12/2002 | DiFoggio | E21B 47/10 73/152.55 |
| 2002/0184940 | A1 * | 12/2002 | Storm, Jr. | G01F 1/8495 73/32 A |
| 2002/0194906 | A1 * | 12/2002 | Goodwin | E21B 49/08 73/152.46 |
| 2003/0033870 | A1 * | 2/2003 | Shah | G01N 29/11 73/299 |
| 2004/0150296 | A1 * | 8/2004 | Park | G01N 29/022 310/324 |
| 2004/0194548 | A1 * | 10/2004 | Dayagi | C07C 323/60 73/580 |
| 2004/0244487 | A1 * | 12/2004 | Kolosov | G01N 29/022 73/570 |
| 2005/0182566 | A1 * | 8/2005 | DiFoggio | E21B 47/10 702/11 |
| 2006/0032301 | A1 * | 2/2006 | DiFoggio | E21B 49/081 73/152.18 |
| 2006/0243032 | A1 * | 11/2006 | Liu | G01N 11/00 73/53.05 |
| 2007/0059212 | A1 * | 3/2007 | Masters | G01N 29/036 422/88 |
| 2007/0095153 | A1 * | 5/2007 | Rieder | G01F 1/8413 73/861.356 |
| 2009/0100925 | A1 * | 4/2009 | DiFoggio | E21B 47/10 73/32 A |
| 2011/0138878 | A1 * | 6/2011 | Serban | G01N 29/022 73/24.02 |
| 2011/0167910 | A1 * | 7/2011 | Storm | G01F 1/74 73/32 A |
| 2011/0303012 | A1 | 12/2011 | Amundsen et al. | |
| 2013/0180330 | A1 | 7/2013 | Gao et al. | |
| 2013/0333882 | A1 * | 12/2013 | Stukan | E21B 43/162 166/252.5 |
| 2015/0075279 | A1 * | 3/2015 | Donzier | G01N 9/002 73/32 A |
| 2015/0111765 | A1 * | 4/2015 | Laury-Kleintop | G01N 29/022 506/9 |
| 2015/0160165 | A1 * | 6/2015 | Murphy | G01N 29/022 73/23.34 |
| 2015/0253231 | A1 | 9/2015 | Gao et al. | |
| 2016/0108729 | A1 | 4/2016 | Li et al. | |
| 2016/0326866 | A1 * | 11/2016 | Swett | B06B 1/0614 |
| 2016/0370325 | A1 * | 12/2016 | Yusuf | G01N 29/032 |
| 2017/0205532 | A1 * | 7/2017 | Shen | G01N 21/66 |
| 2017/0285211 | A1 * | 10/2017 | Monteiro | G01V 3/24 |
| 2018/0202976 | A1 * | 7/2018 | Saji | G01N 29/022 |

OTHER PUBLICATIONS

Sauerbrey, "Verwendung von Schwingquarzen zur Wagung dunner Schichten and zur Mikrowagung," Zeitschrift fur Physik (1959) 155 (2): 206-222.

Stanford Research Systems, "QCM100—Quartz Crystal Microbalance Theory and Calibration," Stanford Research Systems, downloaded from http://www.thinksrs.com/downloads/PDFs/ApplicationNotes/QCMTheoryapp.pdf.

Srivastava et al., Quartz-crystal microbalance study for characterizing atomic oxygen in plama ash tools, J. Vac. Sci. Technol. A 19(1), 97-100 Jan./Feb. 2001.

International Search Report and Written Opinion from PCT/US2016/054723, dated Jun. 14, 2017.

* cited by examiner

FREQUENCY SENSORS FOR USE IN SUBTERRANEAN FORMATION OPERATIONS

BACKGROUND

The embodiments herein relate generally to apparatus and methods for use in subterranean formation operations and, more particularly, to frequency sensors and methods of use thereof for detecting analytes in subterranean formation operations.

Hydrocarbon fluids, including oil and natural gas, are obtained from wellbores drilled into subterranean formations (or simply "formations") having hydrocarbon-rich reservoirs. After the wellbore is drilled, it is completed by installation of specially designed equipment and materials to facilitate and control hydrocarbon production. At any point during the design, drilling, and completion of a particular wellbore, it may be desirable to obtain certain information about the characteristics of the produced fluids from the formation. As used herein, the term "produced fluids," and grammatical variants thereof, refers to, any fluid recovered to the surface from a wellbore that is not an introduced treatment fluid (i.e., not a fluid that was placed into the wellbore). Accordingly, produced fluids may be oil, gas, water, and the like.

It may be desirable to determine whether deleterious materials (e.g., corrosive materials, metallurgic reactant materials, and the like). Such deleterious materials can affect equipment and/or operators involved in upstream, midstream, and downstream oil and gas sectors. As used herein, the "upstream" sector refers to exploration and production of crude formation fluids; the "midstream" sector refers to transportation and storage of crude formation fluids; and the "downstream" sector refers to refinement of crude formation fluids, including processing and purifying raw natural gas.

BRIEF DESCRIPTION OF THE DRAWINGS

The following figures are included to illustrate certain features and inventive aspects of the embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
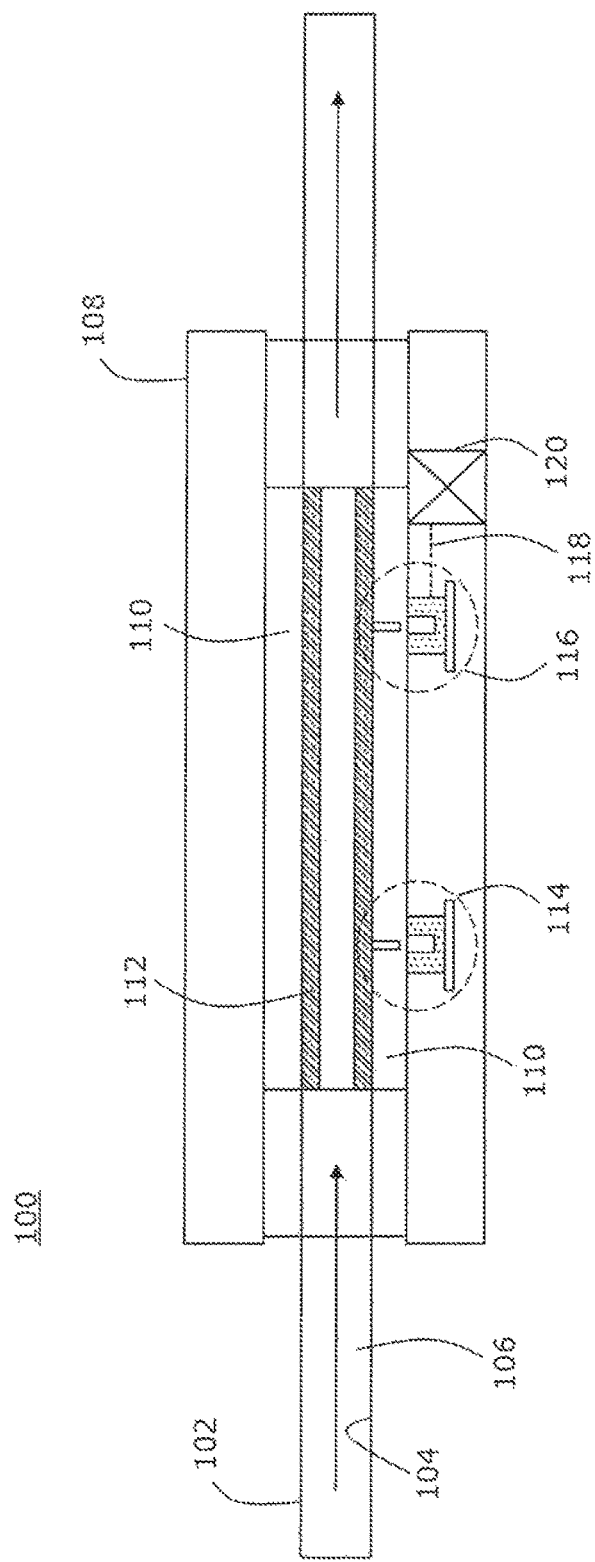
FIG. 1 depicts a cross-sectional view of a frequency sensor, according to one or more embodiments of the present disclosure.

The embodiments herein relate generally to apparatus and methods for use in subterranean formation operations and, more particularly, to frequency sensors and methods of use thereof for detecting analytes in subterranean formation operations. Specifically, the frequency sensors of the present disclosure synergistically combine a vibratable flow tube having a reactant sensitive to an analyte of interest functionalized thereto. The frequency sensor is able to detect a frequency shift corresponding to the presence of the analyte that has reacted with the reactant in real-time or near real-time. The frequency shift can respond, for example, to the change in mass, or density, of a particular reactant once it has reacted with the analyte. For example, the frequency shift to increased mass of the reactant (e.g., by absorption of an analyte) drives a decrease in frequency, and vice versa. As previously mentioned, the frequency sensors described herein may be employed at any point during the design, drilling, and completion of a particular wellbore to obtain information about a particular analyte.

The embodiments herein employ frequency sensors for detection of an analyte of interest within a formation fluid, including deleterious material analytes, which are of particular interest. As used herein, the term "fluid" refers to liquid phase and gaseous phase substances. As used herein, the term "analyte," and grammatical variants thereof, refers to a material (or substance) whose chemical and/or physical attributes are being qualitatively and/or qualitatively detected. Although the embodiments described herein are described with reference to detecting potentially deleterious analytes, it is to be appreciated that non-deleterious analytes may also be detected and/or measured in accordance with the embodiments of the present disclosure.

The frequency sensors described herein may be used in upstream, midstream, or downstream processes and/or equipment, without departing from the scope of the present disclosure. For example, the frequency sensor(s) may be employed in a downhole formation testing tool within a wellbore that collects, monitors, analyzes, and/or brings formation fluid samples to surface. Such formation testing tools are sealed tools that typically contain a passage or flow channel that is used to withdraw fluid directly from the formation. The formation fluid is collected within the tool and analyzed in the wellbore using the frequency sensors described herein, and can additionally be brought to the surface for duplicate or further analysis, which may or may not employ the frequency sensors described herein. The frequency sensor may be located within a formation testing tool in an oil fluid stream, a gas fluid stream, and/or an aqueous fluid stream at a downhole location (e.g., a hydrocarbon producing wellbore, a mining operation, a remedial contaminated groundwater operation, and the like). In some embodiments, the formation testing tool may be part of a wireline system used during a drilling application, for example, for conveying the data received from the frequency sensor to the surface for monitoring. Such wireline systems are described in greater detail below. The frequency sensors may further be employed in transport and storage equipment (e.g., a pipeline, a truck, a rail car, an oil tanker, a barge) for conveying the formation fluid to one or more locations or for maintaining it at a particular location, and in which the formation fluid comes into contact. Additionally, the frequency sensors may be utilized in processing, refining, and purifying equipment that contacts the formation fluid. Accordingly, the frequency sensors may be located in an oil fluid stream or a gas fluid stream at one or more surface locations, such as a fluid stream forming part of a chemical plant.

In some embodiments, the frequency sensor may be used at one or more locations during any or all of upstream, midstream, and downstream sector operations or processes. In such a manner, for example, one or more desired analytes can be monitored throughout all or a portion of a formation fluids lifetime prior to delivery to an end-user. Moreover, interactions with specific equipment can be pinpointed or otherwise elucidated that result in increasing or decreasing levels of one or more desired analytes.

As previously mentioned, deleterious analytes may be particularly desirable to detect in formation fluids. For example, mercury present in formation fluid (e.g., in a gaseous stream from a formation, such as a pipeline, storage equipment, or processing equipment) can result in metallurgical equipment failures (e.g., heat exchange equipment) due to amalgamation of the equipment surfaces with the mercury in the formation fluid. Such amalgamation may cause equipment failure or reduce the efficacy or efficiency of the equipment. Indeed, in some instances, formation fluids can produce upwards of 500 grams (g) of elemental mercury per day (e.g., gas fields in Malaysia, Thailand, and Australia), which can significantly affect equipment, operations, and costs. As another example, hydrogen sulfide ($H_2S$) present in formation fluid can result in environmental, health, and safety concerns. Hydrogen sulfide is extremely poisonous, corrosive, flammable, and explosive. It can cause stress corrosion cracking when combined with water, resulting in micro-cracks in metal equipment that reduces the metals tensile stress (and thus the stress at which it may fail). Other analytes of interest include, but are not limited to, a salt, carbon dioxide, solid particulates, and any combination thereof, as discussed in greater detail below.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and from time to time. While a developer's efforts might be complex and time-consuming, such efforts would be, nevertheless, a routine undertaking for those of ordinary skill in the art having benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, properties such as molecular weight, reaction conditions, and so forth used in the present specification and associated claims are to be understood as being modified in all instances by the term "about." As used herein, the term "about" encompasses +/−5% of a numerical value. For example, if the numerical value is "about 80%," then it can be 80%+/−5%, equivalent to 76% to 84%. Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "substantially" means largely, but not necessarily wholly.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure, the uphole direction being toward the surface of the well and the downhole direction being toward the toe of the well.

Referring now to FIG. 1, illustrated is a cross-sectional view of a frequency sensor, according to one or more embodiments of the present disclosure. As shown, frequency sensor 100 comprises a vibratable flow tube 102 (or simply "flow tube 102") having an interior 104. The interior 104 defines flow bore 106 through which fluid can flow (arrows). Although the flow tube 102 is shown as having a horizontal (or straight) configuration, it is to be appreciated that other configurations for the flow tube 102 may be utilized in accordance with the embodiments described herein (e.g., vertical, deviated (slanted), S-shaped, C-shaped, U-shaped, D-shaped spiral-shaped, and the like), without departing from the scope of the present disclosure. Selection of the particular configuration of the flow tube 102 will depend on a number of factors including, but not limited to, the direction of fluid flow, the location in which the frequency sensor 100 is placed (e.g., downhole, a pipeline, and the like), and the like, and any combination thereof. Preferred shapes for theoretical modeling and data interpretation may include horizontal (or straight) configurations and U-shaped configurations. The flow tube 102 may be encased or otherwise supported by a housing 108 that can be made of a rigid material that not only provides support to the flow tube 102, but also aids in isolating a vibrating region 110. In some embodiments, as shown, an annular area is formed in the vibrating region 110 between the flow tube 102 and the housing 108.

Within the vibrating region 110, at least a portion of the interior 104 of the flow tube 102 is functionalized with a reactant 112 sensitive to an analyte of interest in a fluid (e.g., a formation fluid) for detection based on a frequency shift by the frequency sensor 100, as described below. As used herein, the term "at least a portion" with reference to functionalization of the interior 104 of the flow tube 102 with a reactant 112 refers to at least about 0.1% of the surface of the interior 104 in the vibrating region 110 being functionalized with the reactant 112. That is, at least about 0.1% of the interior 104 of the flow tube 102 is functionalized with reactant 112, up to (as shown) 100% of the interior 104 of the flow tube 102 is functionalized with reactant 112. The portion of the vibrating region 110 being functionalized with the reactant 112 may be determined based on the desired target sensitivity and longevity of the sensor, taking into account resolution in frequency measurement, the mass change in reactant and analyte interaction, and the like.

Figure 2:
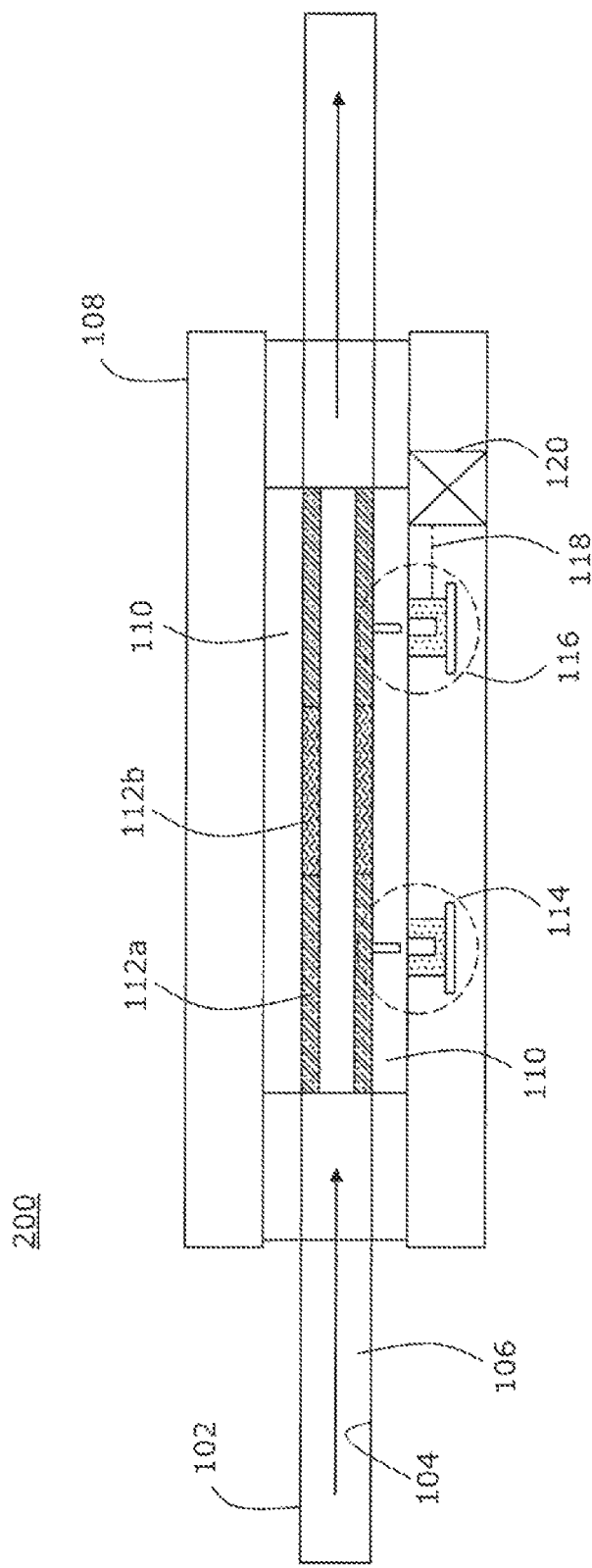
FIG. 2 depicts a cross-sectional view of a frequency sensor functionalized with two reactants, according to one or more embodiments of the present disclosure.

Referring now to FIG. 2, with continued reference to FIG. 1, illustrated is frequency sensor 200, which is substantially similar to frequency sensor 100 of FIG. 1, except that two reactants 112a, 112b are functionalized onto the interior 104 of flow tube 102. Accordingly, each of the two reactants 112a, 112b are sensitive to a different analyte and the frequency sensor 200 detects two frequency shifts associated with each of the two reactants 112a,b, and the measurement circuitry 120 determines frequency shifts corresponding to each single analyte, as described below. It is to be appreciated that although FIG. 2 depicts two reactants 112a, 112b, a plurality (two or more) of reactants may be functionalized onto the interior 104 of the flow tube 102, without departing from the scope of the present disclosure. Moreover, the plurality of reactants may be functionalized onto the interior 104 of the flow tube 102 in any configurations, including a spaced-apart configuration (as shown) or a random configuration, and the amount of any one reactant may be more, less, or the same in amount compared to any other reactant. The configuration and amount of any particular reactant will depend on, at least in part, the particular type and amount of analytes expected to be encountered in a particular fluid (e.g., formation fluid).

It is to be appreciated that the frequency shift sensitivity may be compromised where a plurality of reactants are used with a single frequency sensor, and reactants expected to have very different frequency shifts may be preferable. In some embodiments, the frequency shift measurement together with measurement of the mode shape of vibration can be used to differentiate reactants, or a very thin-massed flow tube material is used (e.g., graphene, carbon nanotubes, and the like), to enhance sensitivity where a plurality of reactants are used in a single frequency sensor. The reactive area within the flow tube can be used to accentuate a mode shape and a sensitivity to an analyte. In other embodiments, the sensitivity can be enhanced by coating each of the different reactants at known portions of the flow tube 102 in the vibrating region 110 to depress and enhance various features of the frequency spectra. For example, if the reactant 112a can be coated at a ¼ portion of the flow tube 102 and a ⅓ portion of the flow tube 102 in the vibrating region and the reactant 112b at known portions adjacent thereto or therebetween.

Referring back to FIG. 1, the flow tube 102 is composed of any material capable of vibrating and capable of having a reactant 112 functionalized thereto. In some embodiments, the flow tube 102 is composed of a plastic, a metal, a ceramic, a glass, and any combination thereof. That is, the flow tube 102 may be composed of a composite material of two or more of a plastic, a metal, or a ceramic. In such instances, the properties of the individual materials retain their specific characteristics, but can be used to synergistically enhance the properties of the flow tube 102, such as by enhancing functionalization of the reactant 112 thereon. For example, the flow tube 102 may be a composite material of ceramic fibers embedded in a metal or polymer matrix. In some specific embodiments, for example, the flow tube 102 is composed of graphene, carbon nanotubes, fiber glass, graphite, a graphite composite, a carbon-fiber reinforced polymer, polyether ether ketone, an organic polymer, epoxy, ceramic (e.g., aluminum oxide, a nitrogen doped aluminum oxide, and the like), and any combination thereof. In some embodiments, the flow tube 102 is one of fiber glass, graphite, a graphite composite, a carbon-fiber reinforced polymer, polyether ether ketone, an organic polymer, epoxy, ceramic, and any combination thereof coated with graphene, carbon nanotubes, and any combination thereof. The selection of the particular type of material for forming the flow tube 102 depends, at least in part, on the analyte of interest to be detected, the reactant 112 to be functionalized thereto, the functionalization method selected, and the like, and any combination thereof.

The reactant 112 selected to be functionalized on the interior 104 of the flow tube 102 is selected based on the analyte of interest in the fluid to be examined, where the reactant 112 reacts with the analyte in some manner. For example, the analyte may react with the reactant 112 by degrading (or dissolving) the reactant 112, by absorbing the analyte to the reactant 112, by wearing away (or eroding) the reactant 112, and the like. Analytes of interest may be any compound or particulate present in a fluid (e.g., a formation fluid) of interest. For example, the analyte may be a corrosive compound, a gas of interest (e.g., carbon dioxide considered a greenhouse gas whose identification and capture may be desirable), a compound signifying a process failure (e.g., particulate erosion of the reactant 112 signifying a screen break), and the like. Examples of suitable analytes include, but are not limited to, hydrogen sulfide, mercury, salt, carbon dioxide, solid particulates, biological molecules, microorganisms, and any combination thereof.

Examples of reactants 112 that can be functionalized on the interior 104 of the flow tube 102 that are sensitive to analytes in a fluid include, but are not limited to, gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof. As used herein, the term "alloy" is a metal made by combining two or more metallic elements, where at least 50% of the alloy comprises the named metal (e.g., a gold alloy comprises at least 50% gold). As examples of reactant-analyte pairings, gold, gold alloys, precious metals (e.g., gold, silver, platinum, palladium, ruthenium, rhodium, osmium, iridium), sulfur-limonene polysulfide, and piezoelectric crystals are sensitive to mercury; and frangible materials are sensitive to solid particulates; noble metals (e.g., ruthenium, rhodium, palladium, silver, osmium, iridium, platinum, gold, mercury, rhenium) alloyed with iron are sensitive to hydrogen sulfide; antibodies are sensitive to biological molecules and microorganisms.

The reactants 112 described herein are functionalized to the interior 104 of the flow tube 102 by any means suitable for the two materials. Specific examples of functionalization methods include, but are not limited to, adhering the reactant 112 to the interior 104 (e.g., with an adhesive such as a resin, a tackifying agent, a glue, and the like), mechanically attaching the reactant 112 to the interior 104 (e.g., with a mechanical fastener such as a clamp, a latch, a spring connection, a crew, a bolt, a nail, and the like), brazing the reactant 112 to the interior 104 (e.g., by soldering with a metal or alloy, such as a copper-zinc alloy, at high temperature), welding the reactant 112 to the interior 104 (e.g., joining together by heating the surfaces to a melting point), chemical deposition of the reactant 112 to the interior 104, and any combination thereof. The chemical deposition of the reactant 112 to the interior 104 may be by any means compatible with the reactant 112 and the material forming the interior 104 of the flow tube 102 to permit functionalization. Specific examples of chemical deposition methods include, but are not limited to, nickel plating, electrodeless nickel plating, electroplating, chemical vapor deposition, atomic layer deposition, precipitation, and the like, and any combination thereof.

In some embodiments, as shown, the measurements may be taken as fluid flows through the flow tube 102 in the vibrating region 110. In other embodiments, the housing may be configured to completely isolate a portion of fluid within the flow tube 102 in the vibrating region 110 to obtain measurements for a particular period of time. For example, the housing 108 can be equipped with end bulkheads that are capable of forming a dividing wall or barrier to retain a portion of fluid within the vibrating region 110, which is later released (e.g., a sliding door mechanism, a swinging door mechanism, a valve, and the like), without departing from the scope of the present disclosure.

The frequency sensor 100 detects the analyte by a frequency shift formed from reacting with the reactant 112. To this end, in some embodiments, the frequency sensor 100 includes a vibration source 114, a vibration detector 116, and measurement circuitry 120. The vibration source 114 is coupled to the flow tube and configured to excite vibration of the flow tube 102 in the vibrating region 110. As used herein, the term "coupled," and grammatical variants thereof, includes both an indirect or direct connection. In certain embodiments, the vibration source 114 may be an electromagnetic hammer used to strike the flow tube 102 in the vibrating region 110, a magnetic field (e.g., where the flow tube 102 is placed within the magnetic field and alternative currents pass therethrough), a mechanical shaker, an acoustic frequency generator, and any combination thereof.

The frequency sensor 100 comprises a vibration detector 116 coupled to the flow tube 102 in the vibrating region 110. The vibration detector 116 detects at least one frequency at a specific time or over time of a fluid in the flow tube 102 in the vibrating region 110. The vibration detector 116 may be any device or object capable of detecting frequency and capable of being communicably coupled to measurement circuitry 120, which is able to analyze the detected frequencies from the vibration detector 116, such as frequency shifts associated with the reaction of the analyte and the reactant 112. Examples of suitable vibration detectors include, but are not limited to, a metallic wire, a fiber optic (e.g., an optical sensor), a strain gauge, an accelerometer, a piezoelectric sensor, a magnet-voice coil, a displacement sensor, and any combination thereof. As examples, if the vibration detector 116 is a fiber optic, the vibration detected can be light reflected off the vibrating flow tube 102 in response to the analyte and reactant 112 reacting; if the vibration detector 116 is an accelerometer, the vibration detected can be acceleration or deceleration of the vibrating flow tube 102 in response to the analyte and reactant 112 reacting; of if the vibration detector 116 is a displacement sensor, the vibration detected can be sound generated by the vibrating fluid tube 102 in response to the analyte and reactant 112 reacting.

Although the location of the vibration source 114 in FIG. 1 (and FIG. 2) is upstream of the vibration detector 116, it is to be appreciated that the vibration source 114 (when integral to the frequency sensor 100) and the vibration detector 116 may be in any configuration relative to each other, provided that the vibration source 114 is able to excite vibration of the flow tube 102 in the vibrating region 110 and the vibration detector 116 is able to detect vibration frequency in the vibrating region 110, without departing from the scope of the present disclosure.

The vibration detector 116 is communicably coupled to measurement circuitry 120 via communication line 118. As shown, the measurement circuitry 120 is integral to the housing 108; however, it is to be appreciated that the measurement circuitry 120 may be communicably coupled to the vibration detector 116 via communication line 118 without the measurement circuitry 120 being integral to the frequency sensor 100 (including the housing 108), such as where the measurement circuitry is a separate component that connects to the frequency sensor 100 via the communication line 118, without departing from the scope of the present disclosure. The communication line 118 is an electrical connection, which may be wired or wireless, which permits communication between the vibration detector 116 and the measurement circuitry 120 such that the measurement circuitry 120 can analyze the frequencies detected by the vibration detector 116. The measurement circuitry 120 determines at least a frequency shift corresponding to the presence of the analyte due to the reaction of the analyte with the reactant 112. That is, the vibrating flow tube 102 having the reactant 112 functionalized thereon and unreacted has a particular frequency, wherein the reaction of the reactant 112 with the analyte in a fluid in the flow tube 102 results in a different frequency, which may be either greater or lesser than the unreacted frequency. The measurement circuitry 120 measures this frequency shift, and such frequency shift corresponds to one or more of a characteristic of the analyte including, but not limited to, a mass of the analyte, a concentration of the analyte, a diffusion coefficient of the analyte, and any combination thereof.

As an example, the measurement circuitry 120 may include a spectral analyzer configured to perform a specific transform on the frequencies (which may be time-based) received by the vibration detector 116. In some embodiments, the measurement circuitry 120 may include a processor designed to execute instructions stored in memory coupled to the processor to perform the transform functions and then later to determine the desired frequency shift associated with the presence of the analyte.

In some instances, the measurement circuitry 120 can be used to measure a frequency shift corresponding to the concentration of the analyte and based on the initial density of the functionalized reactant 112, the final density of the functionalized reactant 112 based on the frequency shift (i.e., after reacting with the analyte). As another example, the measurement circuitry 120 can be used to measure a frequency shift corresponding to the diffusion coefficient of the analyte, where the concentration of the analyte is known by manipulating flow rate (e.g., by ceasing flow rate using bulkheads) in the flow tube 102, where the increase or decrease in the density of the reactant 112 correlates to the diffusion coefficient. In some examples, diffusion coefficient may correlate with the rate at which the frequency shift occurs, and by establishing such correlations, the measurement circuitry 120 can be calibrated for diffusion coefficient measurements. Further, in gases, molecular weight of the gas may be determined; and in liquids, area dimension of the liquid may be determined.

Figure 3:
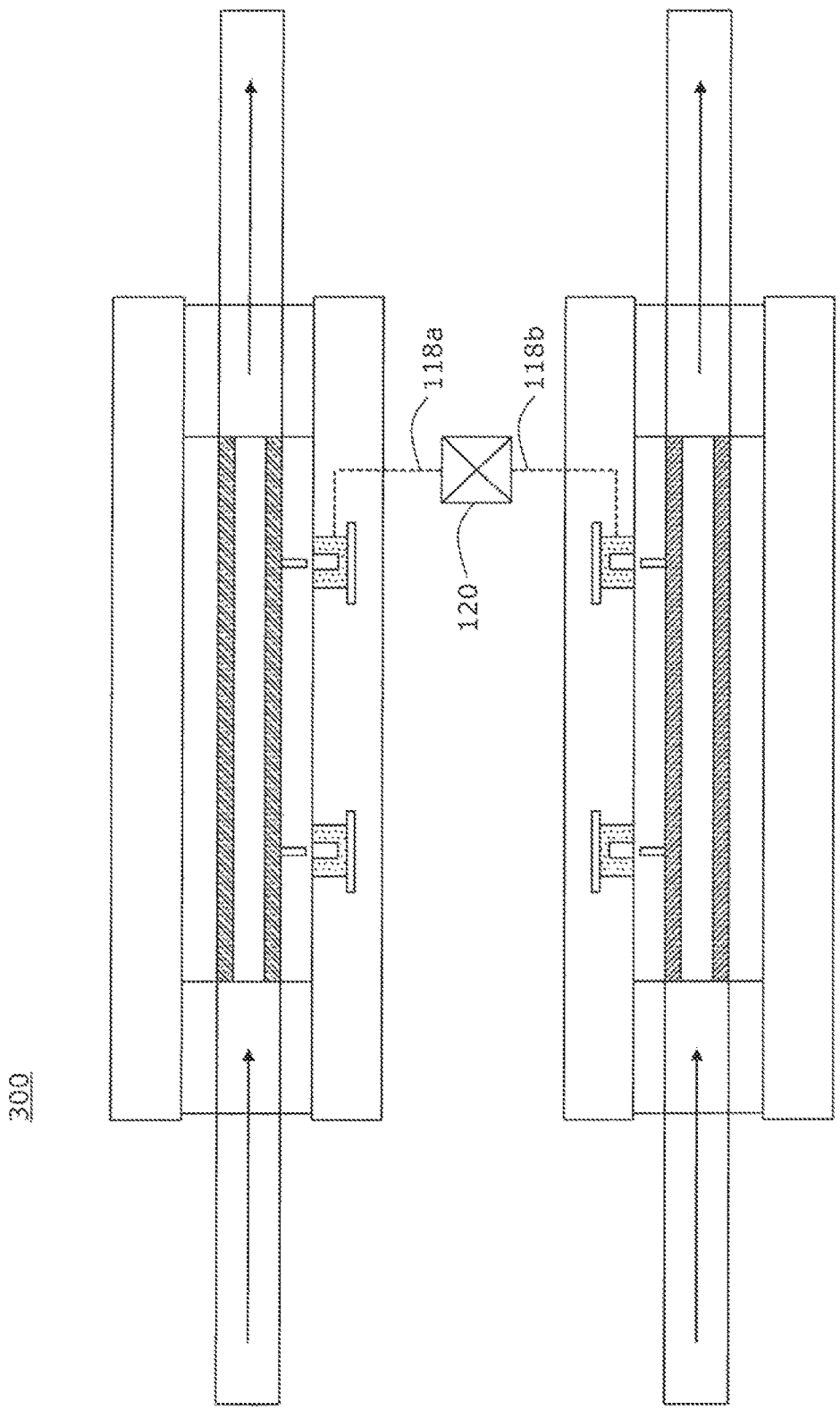
FIG. 3 depicts a cross-sectional view of a frequency sensor system having a pair of frequency sensors each having a vibration detector communicably coupled to measurement circuitry, according to one or more embodiments of the present disclosure.

In another embodiment, two or more frequency sensors 100 are used in tandem to detect a comparative frequency shift between the two sensors. Referring now to FIG. 3, with continued reference to FIG. 1, illustrated is a frequency sensor system 300 having a pair of frequency sensors each having a vibration detector 116 (FIG. 1) communicably coupled to single measurement circuitry 120 via communication lines 118a, 118b each associated with a different frequency sensor. Accordingly, the frequencies detected from both of the frequency sensors can be compared to obtain a comparative frequency shift by the measurement circuitry 120. As used herein, the term "comparative frequency shift" refers to a frequency shift calculated between at least two frequency sensors. In this manner, one or more analytes in a fluid may be detected and analyzed at various points along one or more flow lines or throughout the lifetime of a fluid prior to it being conveyed to an end user (e.g., by wireless communication or wired communication). As one example, a first frequency sensor can be functionalized with a reactant, whereas the second frequency sensor is not functionalized and a comparative frequency shift determined between the two sensors for a particular analyte, or vice versa.

It is to be appreciated that although single measurement circuitry 120 is shown in FIG. 3, each of the individual frequency sensors may comprise individual measurement circuitry that conveys frequency shifts to a separate location for analysis, without departing from the scope of the present disclosure.

For example, in some embodiments, a first frequency is detected using a first frequency sensor and a second frequency is detected using a second frequency sensor. The vibration detectors of each of the first frequency sensor and the second frequency sensor communicate to single measurement circuitry via individual communication lines, where the measurement circuitry determines a comparative frequency shift over time between the first frequency and the second frequency, which corresponds to the present of an analyte having reacted with a reactant. In some instances, as described above, a plurality of reactants are functionalized to the interior of the first and/or second frequency sensor flow tubes, and the measurement circuitry determines frequency shifts corresponding to a single analyte. In some instances, the plurality of reactants is functionalized on a flow tube and a single frequency is detected. In other instances, a plurality of frequency sensors are functionalized on flow tubes having at least one different reactant between the sensors and a combined frequency shift is detected by the vibration detector, and the measurement circuitry is able to parse each frequency shift associated with each particular analyte/reactant pair. In other embodiments, only one of the two frequency sensors has a reactant functionalized to the interior of the flow tube. In yet other embodiments, the two frequency sensors have two different reactants functionalized to the interior of the respective flow tubes.

The vibration detector and measurement circuitry described herein determines frequency shifts related to reaction between a reactant and an analyte using a frequency sensor. Based on the frequency shift, the presence of the analyte is determined, as well as one or more characteristics about the analyte. In other embodiments, such presence and characteristics can be determined based on the reverse, where an analyte that has reacted with the reactant is un-reacted and the frequencies associated with the un-reaction are detected by the vibration detector and the frequency shift determined using the measurement circuitry. For example, where the analyte absorbs onto or into the reactant, thus increasing the mass of the reactant, it can be desorbed (e.g., by heating, and the like) and the decrease in the mass of the reactant is detected as a frequency by the vibration detector, and the frequency shift detected by the measurement circuitry.

As one specific example, the frequency sensor described herein may be functionalized with a reactant sensitive to mercury. As mentioned previously, mercury is a deleterious analyte that will amalgamate with all metal with the exception of iron, although some temperature and pressure may be required for some metals to initiate or accelerate the amalgamation. When mercury is selected as the chosen analyte, as with any analyte, the ideal reactant would be sensitive to mercury over a wide range of temperature and pressure, and be sensitive only to mercury. The sensitivity of the reactant is thus driven by the maximum available analyte, in this case mercury.

In this example, the frequency sensor is thus configured to detect a mercury analyte and the reactant functionalized to the interior of the flow tube of the frequency sensor is gold (e.g., gold film). In the presence of a mercury analyte, the gold reactant would absorb the mercury, thus increasing the mass or density of the gold reactant and lowering the frequency detected by the vibration detector. Additionally, alloying gold with small amounts of metallic sodium will make the amalgamation process of mercury occur both quicker and in the presence of a water film. Over the duration of a downhole operation, then, the amount of mercury present in a formation fluid could be detected using the frequency sensors of the present disclosure by determining the amount of decreased frequency over time. Similarly, as previously discussed, a first frequency sensor may be used that is functionalized with a gold reactant and a second frequency sensor may be used in tandem that is not functionalized with a reactant, where the comparative frequency shift between the two frequency sensors indicates the accumulation of mercury (associated with a lower frequency shift and an increase in mass of the gold reactant on the first sensor). The mercury may further be dissociated with the gold reactant, such as by heating the frequency sensor, where the mercury leaves the amalgam and enters a gas phase. If the two sensor system were used as described above, both frequency sensors could be headed and the mass loss from the gold reactant will be apparent in the comparative frequency shift, and the mass of the mercury could be determined in this manner.

As another specific example, a piezoelectric crystal reactant can be used to detect a mercury analyte. A frequency sensor utilizing a piezoelectric crystal reactant can measure frequency shift using the measurement circuitry based on quartz crystal microbalance (QCM), which is a measurement in a mass variation per unit area by measuring the change in frequency of a quartz crystal resonator (e.g., a piezoelectric crystal). An advantage of QCM is inherently higher frequencies, which translates into shorter counting or measurement times and higher sensitivity and statistical data. Additionally, the smaller mass sensing target (i.e., the piezoelectric crystal reactant) is easier to heat to permit desorption of the mercury analyte, and making the frequency sensor itself more compact.

The sensitivity of QCM based on a frequency shift (a change in oscillation frequency) of a piezoelectric crystal with a reactant having a mass functionalized thereon or thereto can be determined by Equation 1, also known as the Sauerbrey equation:

$$\Delta f = -\frac{2f_0^2}{A\sqrt{\rho_q \mu_q}} \Delta, \qquad \text{Equation 1}$$

where $f_0$ is resonant frequency (unit: Hz), $\Delta f$ is frequency change (units: Hz), $\Delta m$ is mass change (unit: g), A is piesoelectrically active crystal area (the area between electrodes) (unit: $cm^2$), $\rho_q$ is density of the quartz and equal to 2.648 $g/cm^3$), and $\mu_q$ is the shear modulus of quartz for AT-cut crystal equivalent to $2.947 \times 10^{11}$ $g \cdot cm^{-1} \cdot s^{-2}$. Parameters such as volumetric and equilibrium time are parameters determined during measurement using the frequency sensors described herein, and are dependent on mercury concentration and pump out volume from the flow tube.

The QCM is particularly sensitive for frequency shifts ($\Delta f$) of 2% or less, corresponding to a mass change of $2.21 \times 10^{-15}$ grams, assuming a resonant frequency ($f_0$) of 10 MHz. Such sensitivity is adequate for typical mercury concentrations present in formation fluids, for example.

Equation 1 above relates to frequency shift in a gas (e.g., air). The frequency shift in the presence of a liquid (e.g., water or other Newtonian fluid) can be determined by Equation 2:

$$\Delta f = -f_0^{3/2} (\eta_l \rho_l / \rho_q \mu_q)^{1/2} \qquad \text{Equation 2,}$$

where $\eta_l$ is the viscosity of the liquid and $\rho_l$ is the density of the liquid. Corrections may be required to compensate for the density and viscosity of a liquid fluid, which may be done, for example, by using the two frequency sensor described above, where one has one type of QCM and the other a different type with a different resonance, or one is a QCM and the other is not.

Figures 4, 5:
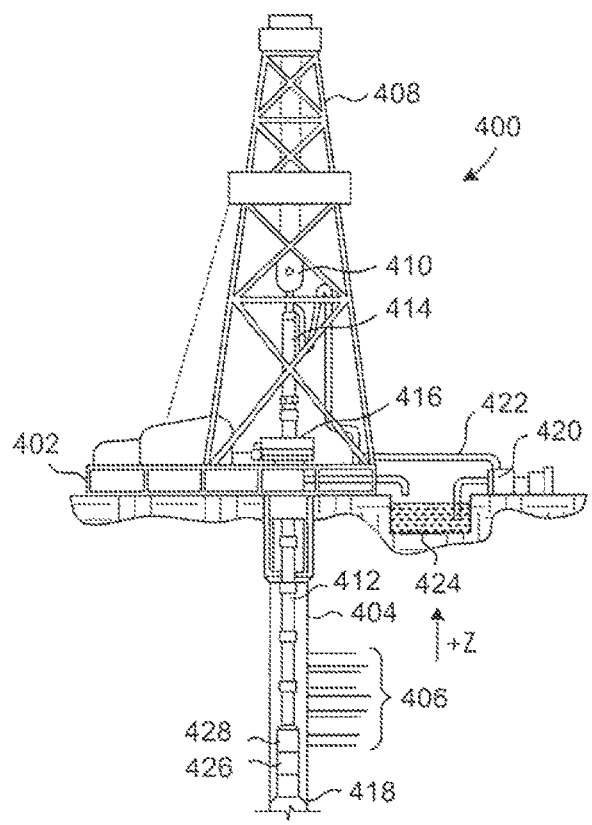
FIG. 4 is a schematic diagram of an exemplary drilling system that may employ the principles of the present disclosure.
FIG. 5 is a schematic diagram of an exemplary wireline system that may employ the principles of the present disclosure.

FIG. 4 is a schematic diagram of an exemplary drilling system 400 that may employ the principles of the present disclosure, according to one or more embodiments. As illustrated, the drilling system 400 may include a drilling platform 402 positioned at the Earth's surface and a wellbore 404 that extends from the drilling platform 402 into one or more subterranean formations 406. In other embodiments, such as in an offshore or subsea drilling operation, a volume of water may separate the drilling platform 402 and the wellbore 404.

The drilling system 400 may include a derrick 408 supported by the drilling platform 402 and having a traveling block 410 for raising and lowering a drill string 412. A kelly 414 may support the drill string 412 as it is lowered through a rotary table 416. A drill bit 418 may be coupled to the drill string 412 and driven by a downhole motor and/or by rotation of the drill string 412 by the rotary table 416. As the drill bit 418 rotates, it creates the wellbore 404, which penetrates the subterranean formations 406. A pump 420 may circulate drilling fluid through a feed pipe 422 and the kelly 414, downhole through the interior of drill string 412, through orifices in the drill bit 418, back to the surface via the annulus defined around drill string 412, and into a retention pit 424. The drilling fluid cools the drill bit 418 during operation and transports cuttings from the wellbore 404 into the retention pit 424.

The drilling system 400 may further include a bottom hole assembly (BHA) coupled to the drill string 412 near the drill bit 418. The BHA may comprise various downhole measurement tools such as, but not limited to, measurement-while-drilling (MWD) and logging-while-drilling (LWD) tools, which may be configured to take downhole measurements of drilling conditions. The MWD and LWD tools may include at least one frequency sensor 426 for determining the presence of an analyte, as described herein.

As the drill bit 418 extends the wellbore 404 through the formation 406, the frequency sensor 426 may collect data related to formation fluids or produced fluids related to the presence of a particular analyte. The frequency sensor 426 and other sensors of the MWD and LWD tools may be communicably coupled to a telemetry module 428 used to transfer measurements and signals from the BHA to a surface receiver (not shown) and/or to receive commands from the surface receiver. The telemetry module 428 may encompass any known means of downhole communication including, but not limited to, a mud pulse telemetry system, an acoustic telemetry system, a wired communications system, a wireless communications system, or any combination thereof. In some embodiments, the telemetry module 428 may be omitted and the drill string 412 may instead comprise wired drill pipe or wired coiled tubing used to transfer data via wired conductors to a surface receiver. In certain embodiments, some or all of the measurements taken by the frequency sensor 426 may be stored within the frequency sensor 426 or the telemetry module 428 for later retrieval at the surface upon retracting the drill string 412.

At various times during the drilling process, the drill string 412 may be removed from the wellbore 404, as shown in FIG. 5, to conduct measurement/logging operations. More particularly, FIG. 5 depicts a schematic diagram of an exemplary wireline system 500 that may employ the principles of the present disclosure, according to one or more embodiments. Like numerals used in FIGS. 4 and 5 refer to the same components or elements and, therefore, may not be described again in detail. As illustrated, the wireline system 500 may include a wireline instrument sonde 502 that may be suspended into the wellbore 404 by a cable 504. The wireline instrument sonde 502 may include the frequency sensor 426, which may be communicably coupled to the cable 504. The cable 504 may include conductors for transporting power to the wireline instrument sonde 502 and also facilitate communication between the surface and the wireline instrument sonde 502. A logging facility 506, shown in FIG. 5 as a truck, may collect measurements from the frequency sensor 426, and may include computing facilities 508 for controlling, processing, storing, and/or visualizing the measurements gathered by the frequency sensor 426. The computing facilities 508 may be communicably coupled to the frequency sensor 426 by way of the cable 504.

It should also be noted that the various drawings provided herein are not necessarily drawn to scale nor are they, strictly speaking, depicted as optically correct as understood by those skilled in spectroelectrochemistry. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Aspects and examples disclosed herein include:

Embodiment/Example A

A frequency sensor comprising: a vibratable flow tube having an interior for receiving a fluid, wherein at least a portion of a surface of the interior is functionalized with a reactant sensitive to an analyte; a vibration detector coupled to the flow tube for detecting a frequency of the fluid received by the flow tube during vibration thereof; and measurement circuitry coupled to the vibration detector for determining a frequency shift over time of the detected frequency, wherein the frequency shift corresponds to the presence of the analyte, the analyte having reacted with the reactant.

Embodiment/Example A may have one or more of the following additional elements in any combination:

Element A1: Wherein the flow tube is vibratable by a vibration source coupled to the flow tube.

Element A2: Wherein the surface of the interior is functionalized with a plurality of reactants sensitive to a plurality of analytes, and a plurality of frequency shifts is determined where each frequency shift corresponds to a single analyte.

Element A3: Wherein the reactant is selected from the group consisting of gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof.

Element A4: Wherein the functionalization of the surface of the interior with the reactant is selected from the group consisting of adhering the reactant to the surface of the interior, mechanically attaching the reactant to the surface of the interior, chemical deposition to the surface of the interior, welding the reactant to the surface of the interior, brazing the reactant to the surface of the interior, and any combination thereof.

Element A5: Wherein the analyte is selected from the group consisting of mercury, hydrogen sulfide, a salt, carbon dioxide, solid particulates, biological molecules, microorganisms, and any combination thereof.

Element A6: Wherein the vibration detector is selected from the group consisting of a metallic wire, a fiber optic, a strain gauge, and any combination thereof.

Element A7: Wherein the frequency shift further corresponds to a characteristic of the analyte, the characteristic selected from the group consisting of a mass of the analyte, a concentration of the analyte, and any combination thereof.

Element A8: Wherein the sensor is located in a formation testing tool.

Element A9: Wherein the sensor is located in an oil fluid stream, a gas fluid stream, or an aqueous fluid stream at a surface location.

Element A10: Wherein the sensor is located in an oil fluid stream, a gas fluid stream, or an aqueous fluid stream at a downhole location in a wellbore.

By way of non-limiting example, exemplary combinations applicable to A include: A1-A10; A2, A4, and A8; A9 and A10; A1, A2, A5, and A7; A3 and A6; A7, A8, and A9; and any other combination of any one or more of A1-A10, without limitation.

Embodiment/Example B

A method comprising: receiving a fluid into an interior of a vibratable flow tube, wherein at least a portion of a surface of the interior is functionalized with a reactant sensitive to an analyte; vibrating the flow tube; detecting a frequency of the fluid received in the interior of the flow tube during vibration thereof with a vibration detector coupled to the flow tube; and determining a frequency shift over time of the detected frequency with measurement circuitry coupled to the vibration detector, wherein the frequency shift corresponds to the presence of the analyte, the analyte having reacted with the reactant.

Embodiment/Example B may have one or more of the following additional elements in any combination:

Element B1: Wherein the flow tube is vibratable by a vibration source coupled to the flow tube.

Element B2: Wherein the surface of the interior is functionalized with a plurality of reactants sensitive to a plurality of analytes, and a plurality of frequency shifts is determined where each frequency shift corresponds to a single analyte.

Element B3: Wherein the reactant is selected from the group consisting of gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof.

Element B4: Wherein the functionalization of the surface of the interior with the reactant is selected from the group consisting of adhering the reactant to the surface of the interior, mechanically attaching the reactant to the surface of the interior, chemical deposition to the surface of the interior, welding the reactant to the surface of the interior, brazing the reactant to the surface of the interior, and any combination thereof.

Element B5: Wherein the analyte is selected from the group consisting of mercury, hydrogen sulfide, a salt, carbon dioxide, solid particulates, biological molecules, microorganisms, and any combination thereof.

Element B6: Wherein the vibration detector is selected from the group consisting of a metallic wire, a fiber optic, a strain gauge, and any combination thereof.

Element B7: Wherein the frequency shift further corresponds to a characteristic of the analyte, the characteristic selected from the group consisting of a mass of the analyte, a concentration of the analyte, and any combination thereof.

Element B8: Wherein the sensor is located in a formation testing tool.

Element B9: Wherein the sensor is located in an oil fluid stream, a gas fluid stream, or an aqueous fluid stream at a surface location.

Element B10: Wherein the sensor is located in an oil fluid stream, a gas fluid stream, or an aqueous fluid stream at a downhole location in a wellbore.

By way of non-limiting example, exemplary combinations applicable to B include: B1-B10; B4, B5, and B7; B3 and B10; B1, B4, B6, and B7; B8 and B10; and any other combination of any one or more of B1-B10, without limitation.

Embodiment/Example C

A method comprising: detecting a first frequency of a fluid with a first frequency sensor comprising: a first vibratable flow tube having an interior for receiving the fluid, wherein at least a portion of a surface of the interior is functionalized with a first reactant sensitive to a first analyte; and a first vibration detector coupled to the first flow tube for detecting the frequency of the fluid received by the first flow tube during vibration thereof; detecting a second frequency of the fluid with a second frequency sensor comprising: a second vibratable flow tube having an interior for receiving the fluid; and a second vibration detector coupled to the second flow tube for detecting the frequency of the fluid received by the second flow tube during vibration thereof; and determining a comparative shift over time between the detected first frequency and the detected second frequency with measurement circuitry coupled to the first vibration detector and the second vibration detector, wherein the comparative frequency shift corresponds to the presence of the first analyte, the first analyte having reacted with the first reactant.

Embodiment/Example C may have one or more of the following additional elements in any combination:

Element C1: Wherein at least a portion of a surface of the interior of the second flow tube is functionalized with a second reactant sensitive to a second analyte, and further comprising detecting a first single shift over time of the detected second frequency with the measurement circuitry, wherein the first single frequency shift corresponds to the presence of the second analyte, the second analyte having reacted with the second reactant.

Element C2: Wherein the first flow tube is vibratable by a vibration source coupled to the first flow tube.

Element C3: Wherein the second flow tube is vibratable by a vibration source coupled to the second flow tube.

Element C4: Wherein the surface of the interior of the first flow tube is functionalized with a plurality of reactants sensitive to a plurality of analytes, and a plurality of frequency shifts is determined where each frequency shift corresponds to a single analyte.

Element C5: Wherein a surface of the interior of the second flow tube is functionalized with a plurality of second reactants sensitive to a plurality of second analytes, and a plurality of frequency shifts is determined where each frequency shift corresponds to a single second analyte.

Element C6: Wherein the first reactant is selected from the group consisting of gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof.

Element C7: Wherein at least a portion of a surface of the interior of the second flow tube is functionalized with a second reactant sensitive to a second analyte, and wherein the second reactant is selected from the group consisting of gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof.

Element C8: Wherein the functionalization of the surface of the interior of the first flow tube with the first reactant is selected from the group consisting of adhering the first reactant to the surface of the interior of the first flow tube, mechanically attaching the first reactant to the surface of the interior of the first flow tube, chemical deposition to the surface of the interior of the first flow tube, welding the first reactant to the surface of the interior of the first flow tube, brazing the first reactant to the surface of the interior of the first flow tube, and any combination thereof.

Element C9: Wherein at least a portion of a surface of the interior of the second flow tube is functionalized with a second reactant sensitive to a second analyte, and wherein functionalization of the surface of the interior of the second flow tube with the second reactant is selected from the group consisting of adhering the second reactant to the surface of the interior of the second flow tube, mechanically attaching the second reactant to the surface of the interior of the second flow tube, chemical deposition to the surface of the interior of the second flow tube, welding the second reactant to the surface of the interior of the second flow tube, brazing the second reactant to the surface of the interior of the second flow tube, and any combination thereof.

Element C10: Wherein the first analyte is selected from the group consisting of mercury, hydrogen sulfide, a salt, carbon dioxide, solid particulates, biological molecules, microorganisms, and any combination thereof.

Element C11: Wherein at least a portion of a surface of the interior of the second flow tube is functionalized with a second reactant sensitive to a second analyte, and wherein the second analyte is selected from the group consisting of mercury, hydrogen sulfide, a salt, carbon dioxide, solid particulates, biological molecules, microorganisms, and any combination thereof.

Element C12: Wherein a vibration detector selected from the group consisting of the first vibration detector, the second vibration detector, and any combination thereof is selected from the group consisting of a metallic wire, a fiber optic, a strain gauge, and any combination thereof.

Element C13: Wherein a sensor selected from the group consisting of the first frequency sensor, the second frequency sensor, and any combination thereof is located in a formation testing tool.

Element C14: Wherein a sensor selected from the group consisting of the first frequency sensor, the second frequency sensor, and any combination thereof is located in an oil fluid stream, a gas fluid stream, or an aqueous fluid stream at a surface location.

Element C15: Wherein a sensor selected from the group consisting of the first frequency sensor, the second frequency sensor, and any combination thereof is located in an oil fluid stream, a gas fluid stream, or an aqueous fluid stream at a downhole location in a wellbore.

By way of non-limiting example, exemplary combinations applicable to C include: C1-C15; C1, C4, C11, and C15; C12 and C13; C2, C5, and C7; C8, C13, and C15; C14 and C15; C10, C12, and C14; and any other combination of any one or more of C1-C15, without limitation.

Therefore, the embodiments disclosed herein are well adapted to attain the ends and advantages mentioned as well as those that are inherent therein. The particular embodiments disclosed above are illustrative only, as they may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A frequency sensor comprising:
   a vibratable flow tube having an interior for receiving a fluid, wherein at least a portion of a surface of the interior is functionalized with a reactant sensitive to an analyte;
   a vibration detector coupled to the vibratable flow tube for detecting a frequency of the fluid received by the vibratable flow tube during vibration thereof; and measurement circuitry coupled to the vibration detector for determining a frequency shift over time of the detected frequency,
wherein the frequency shift corresponds to the presence of the analyte, the analyte having reacted with the reactant.

2. The frequency sensor of claim 1, wherein the vibratable flow tube is vibratable by a vibration source coupled to the vibratable flow tube.

3. The frequency sensor of claim 1, wherein the surface of the interior is functionalized with a plurality of reactants sensitive to a plurality of analytes, and a plurality of frequency shifts is determined where each frequency shift corresponds to a single analyte.

4. The frequency sensor of claim 1, wherein the reactant is selected from the group consisting of gold, silver, copper, iron, nickel, a gold alloy, a silver alloy, a copper alloy, an iron alloy, a nickel alloy, a precious metal, a noble metal, a precious metal alloy, a noble metal alloy, a solid chelating agent, sulfur-limonene polysulfide, a piezoelectric crystal, a salt, a frangible material, an antibody, and any combination thereof.

5. The frequency sensor of claim 1, wherein the functionalization of the surface of the interior with the reactant is selected from the group consisting of adhering the reactant to the surface of the interior, mechanically attaching the reactant to the surface of the interior, chemical deposition to the surface of the interior, welding the reactant to the surface of the interior, brazing the reactant to the surface of the interior, and any combination thereof.

6. The frequency sensor of claim 1, wherein the analyte is selected from the group consisting of mercury, hydrogen sulfide, a salt, carbon dioxide, solid particulates, biological molecules, microorganisms, and any combination thereof.

7. The frequency sensor of claim 1, wherein the vibration detector is selected from the group consisting of a metallic wire, a fiber optic, a strain gauge, and any combination thereof.

8. The frequency sensor of claim 1, wherein the frequency shift further corresponds to a characteristic of the analyte, the characteristic selected from the group consisting of a mass of the analyte, a concentration of the analyte, and any combination thereof.

9. The frequency sensor of claim 1, wherein the frequency sensor is located in a formation testing tool.

10. The frequency sensor of claim 1, wherein the frequency sensor is located in an oil fluid stream, a gas fluid stream, or an aqueous fluid stream at a surface location.

11. The frequency sensor of claim 1, wherein the frequency sensor is located in an oil fluid stream, a gas fluid stream, or an aqueous fluid stream at a downhole location in a wellbore.

12. A method comprising:
receiving a fluid into an interior of a vibratable flow tube, wherein at least a portion of a surface of the interior is functionalized with a reactant sensitive to an analyte;
vibrating the vibratable flow tube;
detecting a frequency of the fluid received in the interior of the vibratable flow tube during vibration thereof with a vibration detector coupled to the vibratable flow tube; and
determining a frequency shift over time of the detected frequency with measurement circuitry coupled to the vibration detector, wherein the frequency shift corresponds to the presence of the analyte, the analyte having reacted with the reactant.

13. The method of claim 12, wherein the vibratable flow tube is vibratable by a vibration source coupled to the vibratable flow tube.

14. The method of claim 12, wherein the surface of the interior is functionalized with a plurality of reactants sensitive to a plurality of analytes, and a plurality of frequency shifts is determined where each frequency shift corresponds to a single analyte.

15. The method of claim 12, wherein the frequency shift further corresponds to a characteristic of the analyte, the characteristic selected from the group consisting of a mass of the analyte, a concentration of the analyte, and any combination thereof.

16. The method of claim 12, wherein the vibratable flow tube is located in a formation testing tool.

17. The method of claim 12, wherein the vibratable flow tube is located in an oil fluid stream, a gas fluid stream, or an aqueous fluid stream at a surface location.

18. The method of claim 12, wherein the vibratable flow tube is located in an oil fluid stream, a gas fluid stream, or an aqueous fluid stream at a downhole location in a wellbore.

19. A method comprising:
detecting a first frequency of a fluid with a first frequency sensor comprising:
a first vibratable flow tube having an interior for receiving the fluid, wherein at least a portion of a surface of the interior is functionalized with a first reactant sensitive to a first analyte; and
a first vibration detector coupled to the first vibratable flow tube for detecting the frequency of the fluid received by the first vibratable flow tube during vibration thereof;
detecting a second frequency of the fluid with a second frequency sensor comprising:
a second vibratable flow tube having an interior for receiving the fluid; and
a second vibration detector coupled to the second vibratable flow tube for detecting the frequency of the fluid received by the second vibratable flow tube during vibration thereof; and
determining a comparative shift over time between the detected first frequency and the detected second frequency with measurement circuitry coupled to the first vibration detector and the second vibration detector, wherein the comparative frequency shift corresponds to the presence of the first analyte, the first analyte having reacted with the first reactant.

20. The method of claim 19, wherein at least a portion of a surface of the interior of the second vibratable flow tube is functionalized with a second reactant sensitive to a second analyte, and further comprising detecting a first single shift over time of the detected second frequency with the measurement circuitry,
wherein the first single frequency shift corresponds to the presence of the second analyte, the second analyte having reacted with the second reactant.

* * * * *